(12) United States Patent
Sickenberger et al.

(10) Patent No.: US 8,874,377 B1
(45) Date of Patent: Oct. 28, 2014

(54) PHOTON COUNTING BASED PARTICLES DETECTION METHOD AND APPARATUS

(75) Inventors: David W. Sickenberger, Bel Air, MD (US); Richard D. Sickenberger, Silver Spring, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 1064 days.

(21) Appl. No.: 12/380,366

(22) Filed: Feb. 26, 2009

Related U.S. Application Data

(60) Provisional application No. 61/032,615, filed on Feb. 29, 2008.

(51) Int. Cl.
*G01N 33/48* (2006.01)
*G01J 1/58* (2006.01)

(52) U.S. Cl.
USPC .......................................... 702/19; 250/458.1

(58) Field of Classification Search
None
See application file for complete search history.

(56) References Cited

U.S. PATENT DOCUMENTS 7,336,210 B2 * 2/2008 Lazar ........................... 341/110
2006/0231771 A1 * 10/2006 Lee et al. ................... 250/458.1

* cited by examiner

*Primary Examiner* — Anna Skibinski
(74) *Attorney, Agent, or Firm* — Ulysses John Biffoni

(57) ABSTRACT

A method for detecting biological aerosols using a photon counting technique to determine the presence of particles is described. A Schmitt trigger is used to prevent over counting of particle events and for greater stability and noise immunity. An alarm determination is made using time-based statistical data derived from the observed fluorescent and scattered photon data.

16 Claims, 3 Drawing Sheets

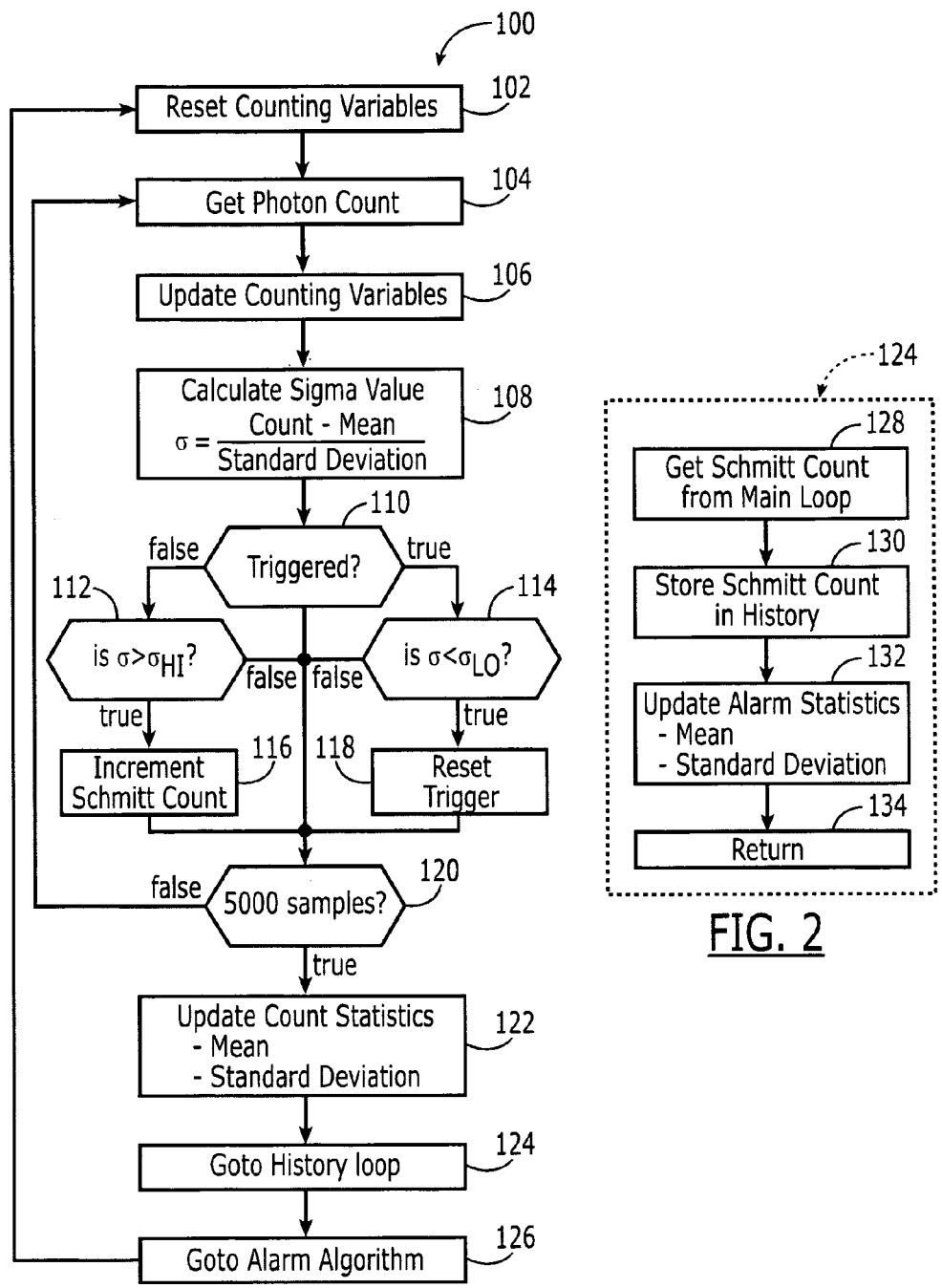

PHOTON COUNTING BASED PARTICLES DETECTION METHOD AND APPARATUS

Figure 3:
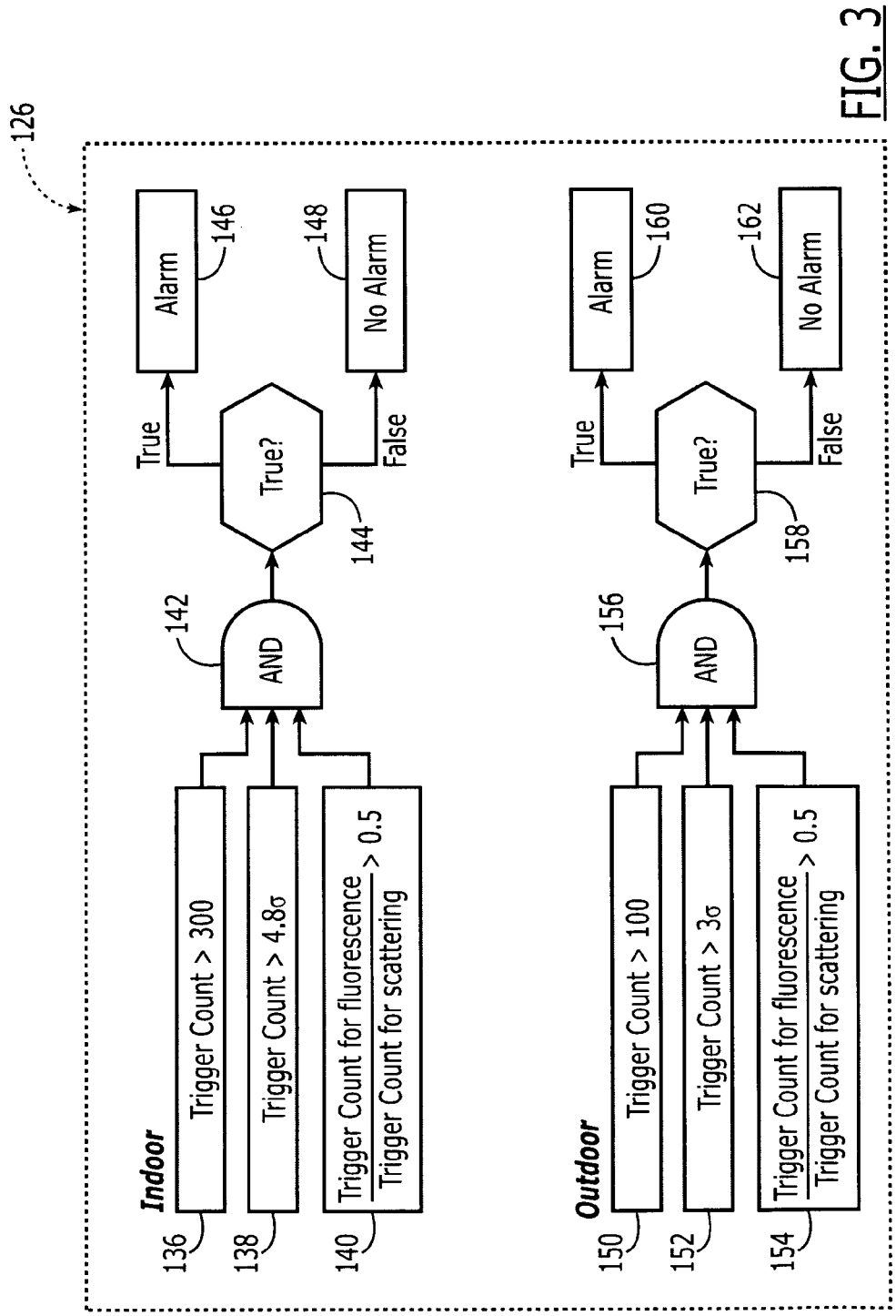

This application claims priority from U.S. Provisional Application Ser. No. 61/032,615, filed Feb. 29, 2008.

GOVERNMENTAL INTEREST

The invention described herein may be manufactured, used and licensed by or for the U.S. Government.

TECHNICAL FIELD

This document relates to detection of aerosols by illumination with ultraviolet radiation.

BACKGROUND

It is well known that biological materials and organisms fluoresce under ultraviolet (UV) light irradiation. UV light in the 380 nanometer (nm) wavelength range, for example, excites biological metabolic products such as Nicotinamide adenine dinucleotide, which is a coenzyme found in most living cells, and flavins, a group of organic compounds based on pteridine, to fluoresce. Higher energy UV, such as light in the 260 nanometer wavelength range, excites proteins. Since vegetative and spoor forms of bacteria contain these biochemicals, the bacteria will also fluoresce when irradiated with UV light. If these biological molecules are present in an aerosol exposed to UV light, they will also scatter part of the excitation light. Both the fluorescent and scattered light can be detected using existing light detectors such as a Photomultiplier Tube (PMT). The presence of both the fluorescent and scattered signal can be used to detect the presence of biological materials or organisms.

Some devices exploit this phenomenon to detect biological aerosol. These detectors typically use a pump to pull in ambient air containing the biological aerosols into some optical interrogation volume. An irradiative UV light, typically from a laser, light emitting diode or xenon lamp, is directed to the particles. The presence of biological particles in the optical interrogation volume will produce fluorescent and scattered photons. These photons are detected using a PMT or equivalent optical detector to produce an electrical signal. The relevant and absolute magnitude of this detected signal can be used to determine the presence of a biological particle. Since differing excitation wavelengths may be used to detect different classes of biological molecules, the excitation wavelength can be chosen to detect specific classes of biological molecules such as proteins, flavinoids, and metabolite products.

A biological aerosol detector of the type described above is described in more detail in U.S. Pat. No. 7,375,348, which is incorporated herein by reference.

Biological aerosol detectors are typically placed in locations where the potential for a biological attack or industrial accident exists. Under operating conditions, these detectors can be expected to continuously collect data for long periods of time, such as days, weeks, or months. The data is expected to consist largely of background signals and events, and to reflect the absence of signal events that indicate the presence of biological particles. To be effective under such operating conditions, biological aerosol detectors must be able to accurately and efficiently detect biological particles in an aerosol sample even when the particles are only present for relatively short periods of time within much longer observation periods.

Biological aerosol detectors typically detect the presence of particles using some form of peak detection algorithm. Peak detection algorithms, as their names imply, detect peaks in a data stream that rise above a background signal level, and that are indicative of signal events. There are a number of challenges in applying existing peak detection algorithms to biological aerosol detection. Photon detectors are susceptible to background noise, there is significant variability across detectors even when the detectors are from the same manufacturer and are of the same model, and detectors drift over time, temperature, and humidity conditions.

Accordingly, what is needed is a method of detecting biological aerosols using a photon counting technique that possesses a greater level of noise immunity, compensates for the variability across detectors, and mitigates detector drift. Also needed is a method to prevent over counting of biological particles that would otherwise result when photon signals produced from a single particle are distributed into more than one sampling bin.

SUMMARY

A method of detecting biological aerosols using a photon counting technique receives two channels of signals, a first channel indicative of a fluorescent photon count and a second channel indicative of a scattered photon count. Each photon count represents the number of photons detected in a time-based sampling bin. The method updates counting variables comprising the mean and standard deviation of photon counts across the sampling bins for each channel; calculates sigma values using the photon count and counting variables for each channel; performs a Schmitt trigger operation using the sigma value and mean to produce a Schmitt trigger count for each channel; counts the number of trigger counts over a set period of time, and alarms when one or more of the trigger counts exceed a specified threshold.

Aspects of the invention may include one or more of the following. A coincident Schmitt trigger may be determined and counted when Schmitt triggers occur at the same time in both channels. The alarm may be conditioned on a Schmitt trigger count that exceeds a specified threshold for the fluorescent channel, scattered channel, coincident count, or any combination thereof. A further condition for an alarm may be that the threshold is defined as a number of standard deviations above the mean. An additional condition may be that the ratio of fluorescent to scattered trigger counts must exceed a threshold.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a flowchart of a method for detecting biological aerosols using a photon counting technique to determine the presence of particles according to an embodiment of the present invention.

FIG. 2 is a more detailed representation of a portion of the method shown in FIG. 1.

FIG. 3 is a more detailed representation of a portion of the method shown in FIG. 1.

FIG. **4*a*** is a plot of photon count data for 21 samples with high and low thresholds illustrated.

FIG. **4*b* is a plot of the Schmitt logic output corresponding to the 21 samples of photon count data of FIG. 4*a***.

DETAILED DESCRIPTION

A method 100 for detecting biological aerosols using a photon counting technique to determine the presence of biological particles is shown in FIG. 1. This process is performed in parallel for both the fluorescent and scattered light signals obtained from a detection device of the type described in U.S. Pat. No. 7,375,348. This process can be applied and utilized with a wide range of other detectors as illustrated by the description below.

At step 102 the counting variables are reset to initial values. Typical counting variables and initial values are provided in reference to Table 1. The photon count for a preset period of time within a sampling bin, such as 200 microsecond (µs) in this illustration, is obtained at step 104. This is also referred to herein as a time-based sampling bin. This choice of sampling duration to define a bin is dependent on both the speed of the signals to be processed as well as the hardware being used. The photon signals are very fast with a full width at half maximum (FWHM) of about 4 nanosecond (ns). In the detection device described in U.S. Pat. No. 7,375,348, current pulses from the scattered and fluorescence PMTs are amplified and converted to a voltage pulse. These signals are not digitized directly to avoid sampling rates in excess of 500 millihertz (MHz). Instead, the voltage pulse is directed towards a comparator which determines that a photon signal is present when a voltage threshold is exceeded. Typical values used for these thresholds are provided below. The comparator output is directed to a digital counter clocked at 1 MHz such that one or more photon signals within a microsecond results in a photon count. This counter is cycled every 200 µs so that the resulting output from both detector channels is the number of photon counts per 200 µs bin.

In this illustration, the process steps in the flowchart of FIG. 1 from step 104 to step 120 are repeated 5,000 times corresponding to 5,000 sample bins. For a 200 µs bin, 5,000 iterations correspond to a total elapsed time of 1 second. These variables can be adjusted for a given device or application by changing either the bin size, the number of samples taken before moving to step 122, or both.

After the photon count is obtained at step 104, the counting variables are updated at step 106 using the new photon count data for the most recent sampling bin. By way of example, the photon count cumulative value is obtained by adding the photon count from the current sampling bin to the previous cumulative value. A value referred to as the sigma value or with the symbol a is then calculated at step 108 based upon the photon count, mean, and standard deviation.

At step 110 a trigger variable is checked to determine if it is set as true or false. That is, the trigger is a binary variable used to perform the logical operation illustrated at step 110. A triggering method, referred to as a Schmitt trigger, is used to prevent over counting of biological particles that would otherwise result when photon signals produced from a single particle are distributed into more than one sampling bin. The Schmitt trigger, which is a comparator with positive feedback, also provides greater stability and noise immunity.

In the case that the trigger is false, the a value is compared to a predefined high threshold value, $\sigma_{HI}$, at step 112. If the a value exceeds the threshold value, $\sigma_{HI}$, the Schmitt count, also referred to herein as the trigger count or Schmitt trigger count, is incremented by one at step 116. If this condition is not satisfied, corresponding to a false outcome at step 112, the Schmitt count remains at its prior value. In the case that the trigger is true, the σ value is compared to the predefined low threshold value, $\sigma_{LO}$, at step 114. If the a value drops below the threshold value, $\sigma_{LO}$, the trigger is reset at step 118 to false. If this condition is not satisfied, corresponding to a false outcome at step 114, the trigger value remains at its current state. As this Schmitt trigger count operation is performed simultaneously for both the fluorescent and scattered photon channels, a coincident Schmitt trigger count can be determined to reflect the number of times that Schmitt triggers occurred in both channels simultaneously. That is, the coincident trigger count is incremented when the trigger counts for both the fluorescent and scattered photon channels are incremented, but is not incremented if either or both of the trigger counts for the two channels are not incremented.

Typical values for $\sigma_{HI}$ are 4 multiples of the standard deviation over the mean for the scattered photon count and 8 multiples of the standard deviation over the mean for the fluorescent photon count. Typical values of $\sigma_{LO}$ are 2 multiples of the standard deviation over the mean for both fluorescent and scattered. These values were determined empirically using the device described in U.S. Pat. No. 7,375,348 under various test conditions.

At step 120, the number of sample iterations representing the processing of individual 200 µs sampling bins is checked. If the number of iterations has yet to reach a predetermined value, which in this illustration is established as 5000 sampling bins, then the operation returns to step 104. If the condition at step 120 is true, corresponding to the processing of the predetermined number of sampling bins, then at step 122 the counting statistics are updated, including the mean and standard deviation.

At step 124, the history function illustrated in FIG. 2 is performed. Upon return from this routine or loop, the alarm function is performed at step 126, which is further illustrated in FIG. 3. Upon completion of the alarm function of step 126, operation is returned to step 102 where the process is repeated.

As will be described more fully below, the logic for alarming is based on the detection of sudden changes or deviations in the trigger counts above given thresholds. The thresholds are determined by averaging the trigger counts with a rolling average over a set time, such as 30 seconds, 1 minute, several minutes, or more. An alarm is based on several conditional events occurring within the same sample time interval, one second in this illustration, in comparison to the historical data. Just as the length of the historical data can be varied, so too can the comparison sample interval by changing either the sample bin size or number or iterations performed as described above.

Turning to FIG. 2, a history loop 124 is illustrated for calculating and storing historical data. At step 128, the current Schmitt count is obtained from the main loop illustrated in FIG. 1. This value of the current Schmitt count is stored in memory at step 130 and alarm statistics are updated at step 132 to include the new mean and standard deviation of the stored Schmitt count data. A history buffer with a predefined size can be used by replacing the oldest Schmitt count value with the newest Schmitt count value once the buffer becomes full. In this way, adequate history data are maintained while limiting the size of the buffer. Performance does not suffer as the older data are less relevant and could even produce an incorrect alarm outcome if kept too long and given the same weight as the more current data. The history loop ends at step 134, returning to the main loop illustrated in FIG. 1.

Turning to FIG. 3, an alarm function 126 is illustrated. Note that trigger count is used in FIG. 3 and elsewhere as a synonymous term for Schmitt count or Schmitt trigger count.

Alarm conditions are provided for both indoor and outdoor applications. As detectors can easily be equipped with a physical or software switch for the user to designate whether the device is being used in an indoor or outdoor environment, both functions can be preset in the device. The user can thus select an indoor or outdoor operating mode without the need for any additional input.

Starting With the illustration for indoor use, at steps 136, 138, and 140, three conditions are established for an alarm to be triggered as follows. The value of one of the trigger counts must exceed a predefined minimum number, such as 300; its value or that of another trigger count must exceed a significant increase over the time-averaged mean at step 138, illustrated here as 4.8σ; and the ratio of trigger counts for fluorescent over trigger counts for scattered must exceed a predefined ratio at step 140, which is illustrated here as 0.5. For example, the trigger count used in step 136 may be the coincident trigger count and the trigger count used in step 138 may be the fluorescent trigger count. This combination aids in preventing the over counting of biological particles that would otherwise result when photon signals produced from a single particle are distributed into more than one sampling bin or as the result of signal noise.

The AND function at step 142 produces a true outcome if all three of these conditions are met and a false outcome otherwise. At step 144, a true outcome from step 142 will trigger the alarm at step 146 while a false outcome will proceed to step 148 for a no alarm condition.

Steps 150, 152, and 154 provide values that are typical for outdoor use. Here, the value of the trigger count for one of the triggers must exceed a similarly predefined minimum number, such as 100; its value or that of another trigger count must exceed a significant increase over the time-averaged mean at step 152, illustrated here as 3σ for the outdoor application; and the ratio of trigger counts for fluorescent over trigger counts for scattered must exceed a predefined ratio at step 154, which is illustrated here as 0.5. The trigger count used in step 150 may be the coincident trigger count and the trigger count used in step 152 may be the fluorescent trigger count. This combination aids in preventing the over counting of biological particles that would otherwise result when photon signals produced from a single particle are distributed into more than one sampling bin or as the result of signal noise. The subsequent process steps of 156, 158, 160, and 162 serve the same function as those described above for the indoor application.

As illustrated above, there are several conditions required to activate an alarm as taught herein. The trigger count must rise quickly compared to the historic background data. A fast increase would typically be expressed as a 3σ change over the mean for an outdoor applications and a 4.8σ change over the mean for indoor applications. The fluorescent and scattered responses must also have a reasonable distribution ratio. For example, if there is an extremely high scattered signal compared to the florescent response, this is typically viewed as an interferent signal and the alarm should therefore be overruled. Finally, the change in trigger count value must exceed some minimal value. This is to prevent false alarms due to extremely small signals corresponding to very clean environments.

Having described the invention above using reference to flowcharts, pseudocode modules are provided in Tables 1-3 to further illustrate the invention.

Table 1 illustrates a pseudocode module for one embodiment of the main loop of the process corresponding to the flowchart of FIG. 1. This loop is executed for both the scattered and fluorescent channels. The following values are based on testing of the device described in U.S. Pat. No. 7,375,348 under various conditions. Typical values found to work well are as follows. For fluorescence data the SigmaHighThreshold is typically established at 8. The SigmaLowThreshold is typically 2 based on observed data. For scattered data, the SigmaHighThreshold is typically 4 and the SigmaLowThreshold is typically 2. The variable n is typically 5000. This represents one second of data with counts provided every 200 microseconds. This value was determined empirically and is also a function of the available memory onboard the central processing unit.

TABLE 1

Main Loop

```
REPEAT
  SET Sum, SumSquared, and SchmittCount to zero
  SET HighLatch to FALSE
  REPEAT
    GET PhotonCount
    Sum ← Sum + PhotonCount
    SumSquared ← SumSquared + PhotonCount^2
    IF Mean and StandardDeviation have been calculated
      Sigma = (PhotonCount − Mean)/StandardDeviation
      IF HighLatch is FALSE
        IF Sigma > SigmaHighThreshold
          SET HighLatch to TRUE
          INCREMENT SchmittCount
        END IF
      ELSE IF HighLatch is TRUE
        IF Sigma < SigmaLowThreshold
          SET HighLatch to FALSE
        END IF
      END IF
    END IF
  UNTIL n sequential PhotonCounts have been read
  Mean ← Sum/n
  StandardDeviation ← sqrt(SumSquared/(n-1) − n/(n-1)*Mean^2)
  GOTO HistoryLoop
UNTIL system is shut down
```

Table 2 illustrates a pseudocode module for one embodiment of the history loop of the process. This corresponds to the flowchart of FIG. 2. The history loop or subroutine is executed for both the scattered and fluorescent channels. The history buffer, once full, contains a set number of data points representing a desired history duration. For example, if the buffer size is set at 30 data points, each representing one second of data, this would represent a 30 second history. As described above, these variables can be varied in a number of ways.

TABLE 2

History Loop

```
GET the SchmittCount from the MainLoop
  IF the HistoryBuffer is full
    Remove the oldest SchmittCount from the history buffer
    Add the new SchmittCount to the history buffer
    Compute the mean (SchmittCountMean) and standard deviation
      (SchmittCountStandardDeviation) of the SchmittCount data in
      the history buffer
    GOTO AlarmAlgorithm
  ELSE
    Add the new SchmittCount to the buffer
  END IF
RETURN to MainLoop
```

Table 3 illustrates a pseudocode module for one embodiment of the alarm function. For indoor applications, typical values found to work well are as follows: MinSchmittCount set at 300; MinSigma set at 4.8; and MinRatio at 0.5. For outdoor applications, typical values found to work well are as follows: MinSchmittCount set at 100; MinSigma set at 3; and MinRatio at 0.5. These values are based on testing of the device described in U.S. Pat. No. 7,375,348 under various conditions.

TABLE 3

Alarm Function.

GET SchmittCount, SchmittCountMean, and
SchmittCountStandardDeviation for fluorescence and scattered channels.
IF SchmittCount >MinSchmittCount
  SET CONDITION 1 to TRUE
ELSE
  SET CONDITION 1 to FALSE
END IF
IF (SchmittCount − SchmittCountMean)/SchmittCountStandardDeviation >
MinSigma
  SET CONDITION 2 to TRUE
ELSE
  SET CONDITION 2 to FALSE
END IF
IF (SchmittCount for fluoresence)/(SchmittCount for scattered) > MinRatio
  SET CONDITION 3 to TRUE
ELSE
  SET CONDITION 3 to FALSE
END IF
IF CONDITIONS 1, 2, AND 3 are all TRUE
  Trigger the alarm
ELSE
  Don't trigger the alarm
END Having illustrated the invention using both flowcharts and pseudocode, sample data are provided in Table 4 below for both the scattered and fluorescence channels as a further illustration. Initially, all of the counting variables (sum, sum squared, and Schmitt count) are set to zero. The Schmitt count, also referred to as trigger count, remains zero for samples 1 through 4 because the sigma value based on the photon count for the sampling bin in both channels is below the specified high threshold.

At sample 5, the sigma value in both channels exceeds the high threshold and increments the respective Schmitt counts. Although the sigma values drop below the high threshold value at samples 6 through 13, the values remain above the low threshold until sample 14. On the 19$^{th}$ sample, the Sigma value for the photon count again exceeds the high threshold and increments the Schmitt count accordingly.

Figure 4A:
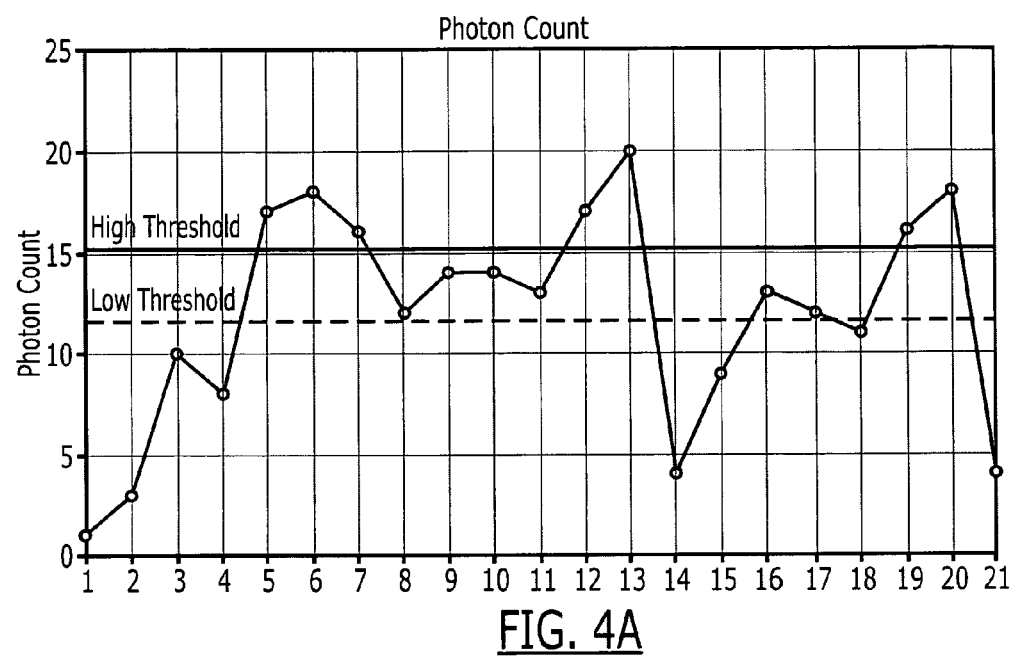
Figure 4B:
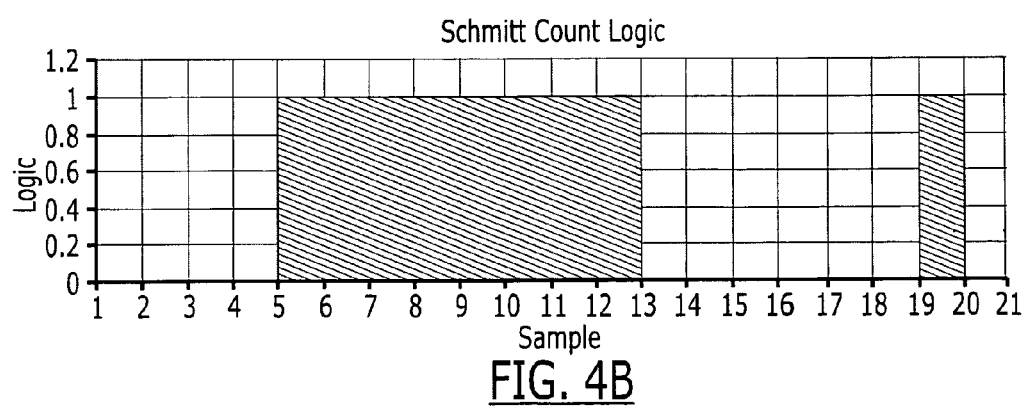

FIGS. 4a and 4b are plots of the photon count data and the corresponding Schmitt logic output, respectively, as provided for the 21 samples from the scattered channel listed in Table 4. The Schmitt logic illustrated by FIG. 4a is zero until sample 5. As shown in the graph of photon counts in FIG. 4A, the count has risen above the high threshold at sample 5, causing the Schmitt logic to be switched to the value 1 or true. It remains at this value until sample 13 because up to that point the photon count remains above the low threshold even though it dropped below the high threshold. The Schmitt count logic remains zero or false as illustrated in FIG. 4b until sample 19 where the photon count as illustrated in FIG. 4a rises above the high threshold. This serves to prevent over counting of biological particles that would otherwise result when photon signals produced from a single particle are distributed into more than one sampling bin. It also provides for greater stability and nose immunity.

TABLE 4

Sample Data

Statistics from previous n Samples:

|  | Scattered | Fluorescence |
| --- | --- | --- |
| Mean | 8.13 | 0.81 |
| Standard Deviation | 1.75 | 2.76 |
| SigmaHighThreshold | 4 | 7 |
| SigmaLowTreshold | 2 | 2 |

Sample Calculations:

| | Scattered | | | | | Fluorescence | | | | |
| --- | --- | --- | --- | --- | --- | --- | --- | --- | --- | --- |
| Sample | Photon Count | Sum | Sum Squared | Sigma | Schmitt Count | Photon Count | Sum | Sum Squared | Sigma | Schmitt Count |
| 1 | 1 | 1 | 1 | −4.1 | | 1 | 1 | 1 | 0.1 | |
| 2 | 3 | 4 | 10 | −2.9 | | 0 | 1 | 1 | −0.3 | |
| 3 | 10 | 14 | 110 | 1.1 | | 1 | 2 | 2 | 0.1 | |
| 4 | 8 | 22 | 174 | −0.1 | | 0 | 2 | 2 | −0.3 | |
| 5 | 17 | 39 | 463 | 5.1 | 1 | 25 | 27 | 627 | 8.8 | 1 |
| 6 | 18 | 57 | 787 | 5.6 | | 21 | 48 | 1068 | 7.3 | |
| 7 | 16 | 73 | 1043 | 4.5 | | 23 | 71 | 1597 | 8.0 | |
| 8 | 12 | 85 | 1187 | 2.2 | | 7 | 78 | 1646 | 2.2 | |
| 9 | 14 | 99 | 1383 | 3.4 | | 9 | 87 | 1727 | 3.0 | |
| 10 | 14 | 113 | 1579 | 3.4 | | 8 | 95 | 1791 | 2.6 | |
| 11 | 13 | 126 | 1748 | 2.8 | | 16 | 111 | 2047 | 5.5 | |
| 12 | 17 | 143 | 2037 | 5.1 | | 21 | 132 | 2488 | 7.3 | |
| 13 | 20 | 163 | 2437 | 6.8 | | 24 | 156 | 3064 | 8.4 | |
| 14 | 4 | 167 | 2453 | −2.4 | | 0 | 156 | 3064 | −0.3 | |
| 15 | 9 | 176 | 2534 | 0.5 | | 0 | 156 | 3064 | −0.3 | |
| 16 | 13 | 189 | 2703 | 2.8 | | 7 | 163 | 3113 | 2.2 | |
| 17 | 12 | 201 | 2847 | 2.2 | | 7 | 170 | 3162 | 2.2 | |
| 18 | 11 | 212 | 2968 | 1.6 | | 1 | 171 | 3163 | 0.1 | |
| 19 | 16 | 228 | 3224 | 4.5 | 2 | 26 | 197 | 3839 | 9.1 | 2 |
| 20 | 18 | 246 | 3548 | 5.6 | | 22 | 219 | 4323 | 7.7 | |
| 21 | 4 | 250 | 3564 | −2.4 | | 0 | 219 | 4323 | −0.3 | |

The invention can be implemented in digital electronic circuitry, or in computer hardware, firmware, software, or in combinations thereof. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in application-specific integrated circuits.

While specific embodiments of the invention have been described, it will be understood that additional embodiments and various modifications may be made without departing from the spirit and scope of the invention. For example, the method is not restricted to use with a particular detector. Thresholds and other values provided in the above illustrations, such as the size and number of sampling bins to use, can be varied. The size of the history buffer can be varied, both in number of stored values and the time represented by each element. Additional or alternative count statistics and thresholds can be used to specify alarm conditions. While the steps of have been described in a particular order, the ordering of certain steps can be rearranged without departing from the spirit and scope of the invention. Accordingly, these and other embodiments of the invention fall within the scope of the following claims.

What is claimed is:

1. A method of detecting biological aerosols using a photon counting technique that processes both fluorescent and scattered photon data, comprising: receiving two channels of signals, a first channel indicative of a fluorescent photon count and a second channel indicative of a scattered photon count, wherein each photon count represents the number of photons detected in a time-based sampling bin; updating counting variables by calculating the sum and sum squared of the photon counts measured across multiple sampling bins for each channel and calculating the mean and standard deviation of photon counts across the sampling bins for each channel; calculating sigma values using the photon count, mean and standard deviation for each channel; performing a Schmitt trigger operation using the sigma value to produce a Schmitt trigger count for each channel; calculating the mean and standard deviation of the Schmitt trigger counts for each channel over a period of time; and triggering an alarm in a biological aerosol detector when a calculated alarm threshold is obtained using said fluorescent and scattered Schmitt trigger counts.

2. The method of claim 1, wherein said Schmitt trigger operation comprises determining the number of increments in the Schmitt trigger count based on when said sigma value exceeds a high value and subsequently returns to a low value.

3. The method of claim 2, wherein said high value comprises 4 multiples of the standard deviation over the mean for the scattered photon count, and 8 multiples of the standard deviation over the mean for the fluorescent photon count.

4. The method of claim 2, wherein said low value comprises 2 multiples of the standard deviation over the mean for both the scattered photon count and the fluorescent photon count.

5. The method of claim 1, wherein said triggering an alarm in a biological aerosol detector when a calculated alarm threshold is obtained using said fluorescent and scattered Schmitt trigger counts comprises triggering the alarm for an indoor detector when the Schmitt trigger count is greater than 300, the Schmitt trigger count exceeds 4.8 standard deviation, and the ratio of the Schmitt trigger count for fluorescence to the Schmitt trigger count for scattering exceeds 0.5.

6. The method of claim 1, wherein said triggering an alarm in a biological aerosol detector when a calculated alarm threshold is obtained using said fluorescent and scattered Schmitt trigger counts comprises triggering the alarm for an outdoor detector when the Schmitt trigger count is greater than 100, the Schmitt trigger count exceeds 3.0 standard deviation, and the ratio of Schmitt trigger count for fluorescence to the Schmitt trigger count for scattering exceeds 0.5.

7. The method of claim 1, wherein said performing a Schmitt trigger operation using the sigma value to produce a trigger count for each channel further comprises calculating a coincident trigger count from the trigger count for each channel.

8. The method of claim 7, wherein said triggering an alarm when a calculated alarm threshold is obtained further comprises the condition that the trigger count must exceed a first threshold for the coincident trigger count and must exceed a second threshold for the fluorescent trigger count.

9. A computer program implemented on non-transitory machine readable medium comprising instructions operable to cause a programmable processor to: receive two channels of signals, a first channel indicative of a fluorescent photon count and a second channel indicative of a scattered photon count, wherein each photon count represents the number of photons detected in a time-based sampling bin; update counting variables by calculating the sum and sum squared of the photon counts measured across multiple sampling bins for each channel and calculate the mean and standard deviation of photon counts across the sampling bins for each channel; calculate sigma values using the photon count, mean and standard deviation for each channel; perform a Schmitt trigger operation using the sigma value to produce a trigger count for each channel; calculate the mean and standard deviation of the Schmitt trigger counts for each channel over a period of time; and trigger an alarm in a biological aerosol detector when a calculated alarm threshold is obtained using said fluorescent and scattered Schmitt trigger counts.

10. The computer program of claim 9, wherein said Schmitt trigger operation comprises determining the number of increments in the Schmitt trigger count based on when said sigma value exceeds a high value and subsequently returns to a low value.

11. The computer program of claim 10, wherein said high value comprises 4 multiples of the standard deviation over the mean for the scattered photon count, and 8 multiples of the standard deviation over the mean for the fluorescent photon count.

12. The computer program of claim 10, wherein said low value comprises 2 multiples of the standard deviation over the mean for both the scattered photon count and the fluorescent photon count.

13. The computer program of claim 9, wherein said triggering an alarm in a biological aerosol detector when a calculated alarm threshold is obtained using said fluorescent and scattered Schmitt trigger counts comprises triggering the alarm for an indoor detector when the Schmitt trigger count is greater than 300, the Schmitt trigger count exceeds 4.8 standard deviation, and the ratio of the Schmitt trigger count for fluorescence to the Schmitt trigger count for scattering exceeds 0.5.

14. The computer program of claim 9, wherein said triggering an alarm in a biological aerosol detector when a calculated alarm threshold is obtained using said fluorescent and scattered Schmitt trigger counts comprises triggering the alarm for an outdoor detector when the Schmitt trigger count is greater than 100, the Schmitt trigger count exceeds 3.0 standard deviation, and the ratio of Schmitt trigger count for fluorescence to the Schmitt trigger count for scattering exceeds 0.5.

15. The computer program of claim 9, wherein said performing a Schmitt trigger operation using the sigma value to produce a trigger count for each channel further comprises calculating a coincident trigger count from the trigger count for each channel.

16. The computer program of claim 15, wherein said trigger an alarm when a calculated alarm threshold is obtained further comprises the condition that the trigger count must exceed a first threshold for the coincident trigger count and must exceed a second threshold for the fluorescent trigger count.

\* \* \* \* \*